United States Patent
Blondeau et al.

(10) Patent No.: US 11,944,727 B2
(45) Date of Patent: Apr. 2, 2024

(54) AIR FRESHENING DEVICE

(71) Applicant: Givaudan S.A., Vernier (CH)

(72) Inventors: Philippe Blondeau, Paris (FR); Sebastien Picci, Kingersheim (FR)

(73) Assignee: GIVAUDAN SA, Vernier (CH)

( * ) Notice: Subject to any disclaimer, the term of this patent is extended or adjusted under 35 U.S.C. 154(b) by 613 days.

(21) Appl. No.: 17/151,332

(22) Filed: Jan. 18, 2021

(65) Prior Publication Data

US 2021/0128770 A1 May 6, 2021

Related U.S. Application Data

(63) Continuation of application No. 15/558,486, filed as application No. PCT/EP2016/055663 on Mar. 16, 2016, now Pat. No. 10,925,992.

(30) Foreign Application Priority Data

Mar. 17, 2015 (GB) .................................. 1504472

(51) Int. Cl.
*A61L 9/03* (2006.01)
*A61L 9/012* (2006.01)

(52) U.S. Cl.
CPC .................. *A61L 9/03* (2013.01); *A61L 9/012* (2013.01); *A61L 2209/135* (2013.01)

(58) Field of Classification Search
CPC .................................. A61L 9/03; A61L 9/012
See application file for complete search history.

(56) References Cited

U.S. PATENT DOCUMENTS

| | | | |
|---|---|---|---|
| 8,716,632 | B1 | 5/2014 | Pesu et al. |
| 2006/0272199 | A1 | 12/2006 | Licciardello et al. |
| 2012/0091218 | A1 | 4/2012 | Mikkelsen et al. |
| 2012/0224995 | A1 | 9/2012 | McMinn |

OTHER PUBLICATIONS

PCT/EP2016/055663—International Search Report, dated Jul. 8, 2016.
PCT/EP2016/055663—International Written Opinion, dated Jul. 8, 2016.

*Primary Examiner* — Sean E Conley
(74) *Attorney, Agent, or Firm* — Curatolo Sidoti & Trillis Co., LPA; Floyd Trillis, III; Salvatore A. Sidoti (57) ABSTRACT

An air freshening device is provided. The device includes a water-based fragrance emitter including water, a water absorbing polymer and a fragrance composition. The fragrance composition includes from about 3% to about 70% by weight of at least one fragrance ingredient exhibiting a standard equilibrium headspace concentration ($HS_i^0$) below about 100 µg/L. The water-based fragrance emitter provides a working signal and an end of life signal upon evaporation. The air freshening device is a warming device.

20 Claims, 3 Drawing Sheets

AIR FRESHENING DEVICE

CROSS REFERENCE TO RELATED APPLICATIONS

This is a continuation application of U.S. Ser. No. 15/558,486, filed on Sep. 14, 2017, which is a national stage application filed under 35 USC 371 of International Application No. PCT/EP2016/055663, filed on Mar. 16, 2016, which applications claim priority to Great Britain Patent Application Serial No. 1504472.0, filed Mar. 17, 2015. The applicant herein incorporates by reference the entirety of each of the foregoing documents herein, and claims all available priority benefit to each of the above applications.

FIELD OF THE INVENTION

The present disclosure relates to air freshening devices. More particularly, the present disclosure relates to air freshening devices including a water-based fragrance emitter and a means for heating the emitter. The air freshening devices are useful in minimizing the amount of residue left in the device after evaporation together with providing a visibly discernable end of life indicator to a user.

BACKGROUND OF THE INVENTION

Systems designed to dispense fragrance materials into ambient air to impart a desirable and pleasant fragrance are well known in the art. Such devices, commonly known as air fresheners or room deodorizers, are commercially available in a variety of forms. A particular type of device is a fragrance warmer, of which a wax warmer is a common variety. Many warmers are designed to be used with "wickless" candles, which are blocks or cubes of scented candle wax with no wick. These devices typically include a power supply, a heating element, scented wax and a plate or container for the scented wax to be contained thereon. These devices are typically powered by mains electricity, batteries or with a tea light or votive candle. In operation, fragrance is evaporated gently from the wax as it melts.

While such a system is elegant in its simplicity and is effective, it suffers from a number of shortcomings. First, wax melts are difficult to clean up. After the fragrance contained in the scented wax is evaporated and before new scented wax is placed in the device, a user needs to remove the wax residues from the plate or container. Because wax stiffens when cooled, it can adhere to many surfaces and prove difficult to remove. Second, these devices do not provide a visibly discernable indicator of the end of the useful life of the scented wax to a user of the device. A hot pool of wax forms that eventually stops throwing fragrance, but a user remains unaware of the need to replace the wax melt. As a result, there is nothing to indicate that new wax melts should be used in the place of the depleted wax melts in order to maintain a consistent fragrance strength/intensity and/or fragrance character during use. This weakening of fragrance strength/intensity and/or character, as well as residual material left in the warming device, have occupied the attention of those who seek to devise better air freshening devices.

Accordingly, there remains a need to provide an air freshening device that does not require the time consuming and messy removal of wax residues and that clearly indicates via a change in a visual characteristic when the fragrance is exhausted.

SUMMARY OF THE INVENTION

In one embodiment, an air freshening device includes a water-based fragrance emitter including water, a water absorbing polymer and a fragrance composition. The fragrance composition includes from about 3% to about 70% by weight of at least one fragrance ingredient exhibiting a standard equilibrium headspace concentration ($HS_i^0$) below about 100 µg/L. The water-based fragrance emitter provides a working signal and an end of life signal upon evaporation of the fragrance composition and water from the emitter and the air freshening device is a warming device.

In another embodiment, an air freshening device includes a water-based fragrance emitter including a fragrance composition having from about 10% to about 35% by weight of at least one fragrance ingredient exhibiting a standard equilibrium headspace concentration ($HS_i^0$) below about 100 µg/L. Upon evaporation, the water-based fragrance emitter is easily removable from the device. The air freshening device is a warming device.

In yet another embodiment, an air freshening device includes a water-based fragrance emitter including a plurality of beads having a water absorbing polymer and a fragrance composition. The fragrance emitter has a fragrance intensity of greater than about 1 on a scale of from zero to five after 5 minutes. The air freshening device is a warming device.

These and other features, aspects and advantages of specific embodiments will become evident to those skilled in the art from a reading of the present disclosure.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

The present disclosure relates to fragrance compositions released by a water-based fragrance emitter into the ambient air and air-freshening devices containing the same. Air freshening devices according to the present disclosure include a water-based fragrance emitter that minimizes the amount of residue left in the air freshening device after evaporation together with a visibly discernable end of life indicator to a user.

Whatever the particular design of the air freshening devices according to the present disclosure, it is imperative that the devices perform in a manner that allows fragrance material to be dispensed at a steady and controlled rate into an environment. Further, substantially all fragrance material should be consumed at the end of the useful life of the emitter or carrier. Further, the amount of residual material remaining after the end of life of the emitter must be minimized and the residual material easily removable, i.e. not sticky, even after a prolonged contact with a hot plate. "Sticky" residue is residue that adheres to a hot plate of the device and requires effort and/or tool for its removal. To the contrary, "non-sticky" residue is residue that is easily removed, using a finger, or a brush or simply by blowing the plate.

In addressing the shortcomings in the art, the applicants surprisingly discovered that replacing wax melts with water based fragrance emitters in a warming device allowed applicant to provide a visibly discernable end of life indicator while at the same time eliminating messy wax residues. Using a heating system imparting temperature gradient induced flows, in combination with a water-based fragrance emitter allows for a much broader selection of suitable fragrance ingredients compared to equivalent passive systems operating at room temperature and relying on diffusion-convection only. In particular, fragrance ingredients that are at the upper end of the molecular weight ranges of available fragrance ingredients can be used, which broadens the creative palette of the perfumer toward typical base notes, allowing olfactive impressions of softness, warmth, solidity and depth, and those particularly that are in the woody, chypre or musk olfactive direction. These olfactive directions are increasingly sought after fragrance ingredients for use in air-freshener devices in order to achieve differentiation in a competitive landscape.

Additionally, applicants have surprisingly found that, using heated water-based fragrance emitters, the rate of fragrance room filling, i.e. the intensity of the smell in the room after a certain time, was significantly faster than that obtained with traditional wax-based fragrance emitters. For example, it was observed that a strong perfume smell was perceived in the room after only a few minutes, for example 2 to 5 minutes, whereas such a benefit is produced only after 10 to 15 minutes or more when using traditional wax-based emitters.

Furthermore, the applicants have found that varying the size of the water-based emitters, it was possible to control the rate of fragrance room filling and the magnitude of this room filling. For example, using smaller water-based fragrance emitters, the rate of room filling was faster and the magnitude of the room filling, i.e. the intensity of the smell in the room after a certain time, for example after one hour, was higher than when using larger water-based fragrance emitters.

The fragrance emitter according to the present disclosure has the advantage of providing two distinct signals to the consumer. A first signal is the gradual transformation of the visual aspect of the emitter, from a transparent gel to an opaque gel, together with a gradual reduction of the size of the emitters, upon evaporation of both fragrance and water. This transformation may be taken by the consumer as the hint that the emitter is working. A second signal is the transformation of the soft emitter into a hard material, occurring after evaporation of the fragrance and water from the emitter. This latter signal can be considered as an unambiguous signal of the end of life of the system. As a result, a user of the air freshening device according to the present disclosure is provided with a clear end of life indicator, whereby the user clearly understands that replacement of the fragrance emitters is required.

Fragrance Emitter

According to the present disclosure, the air freshening devices include a water-based fragrance emitter or carrier. In one embodiment, the fragrance emitter includes a plurality of water beads. For purposes of the present disclosure, water beads also include resin beads and gel beads. In one embodiment, the plurality of water beads may include water, a water absorbing polymer and a fragrance composition.

Water Absorbing Polymer

Suitable water absorbing polymers according to the present disclosure are typically cross-linked hydrophilic polymers, i.e. polymers built up exclusively from water-soluble monomers, or partially hydrophilic polymers, i.e. polymers built up from both water-soluble and water-insoluble monomers. These polymers are also referred to as "super absorbent polymers" (SAPs) or "hydrogels". Super-absorbent polymeric compositions are chemical compositions based on SAPs. SAPs are water-absorbing resins, widely used in sanitary goods, hygienic goods and the like. SAPs are typically lightly cross-linked, to provide for swellability in the presence of water without loss of structural integrity. Typical examples of native natural hydrophilic polymers are alginates, gelatin, dextrans, agar gum, carrageenan gum and gellan gum. Typical examples of modified natural hydrophilic polymers are carboxy methyl cellulose, hydroxyl ethyl cellulose, starch acrylate copolymers, starch acrylonitrile graft copolymers, and the like. Typical examples of synthetic hydrophilic polymers are poly(acrylamide), hydrolyzed poly(acrylamide), monovalent alkaline metal poly (acrylate), such as sodium and potassium polyacrylates, poly(hydroxyethyl methacrylates), poly(vinyl alcohols), sodium poly(vinyl sulfonate), sodium poly(styrene sulfonate), poly(ethylene oxide), poly(vinyl pyrrolidone), poly((meth)acrylic acid) in alkaline media, and the like. Typical partially hydrophilic polymers include poly(acrylamide-co-acrylonitrile), poly(acrylic acid-co-alkyl acrylate), poly((meth)acrylic acid) in acidic media, sodium acrylate/ C10-30 alkyl acrylate crosspolymer or potassium acrylate/ C10-30 alkyl acrylate crosspolymer. Cross-linking is typically performed by co-polymerizing multifunctional monomers, such as alkyl di(meth)acrylate, such as ethylene glycol bis-methacrylate, alkyl tri(meth)acrylate, methylene-bis-acrylamide, divinylbenzene, Di(N-succinimidyl) glutarate, methacrylic anhydride and the like, or by reactive polymer-polymer complex formation, as is the case of gelatin-dextran aldehyde complexes, or non-reactive polymer-polymer complex formation, as is the case of gelatin-gelatin helix formation, alginate-calcium helix formation and the like.

In one embodiment, the water absorbing polymer is a partially cross-linked copolymer of partially saponified (meth)acrylic acid and, optionally, alkyl acrylates and/or hydroxy alkyl acrylates. As a result, the water absorbing polymer consists of loosely cross-linked polyacrylate copolymers bearing carboxylic acid groups, monovalent alkaline metal carboxylate groups and, optionally, alkyl acrylates and/or hydroxy alkyl acrylates. Such polymers are available commercially under different names and brands. In one example, a suitable water absorbing polymer is commercialized under the registered trade mark HISOBEAD® (CAS 9033-79-8, available from Aekyung Specialty Chemicals Ltd.). In another embodiment, the sodium salt of a cross-linked poly(isobutylene-co-maleic anhydride) copolymer (KI-GEL 201K; CAS 39612-00-5, available from Kuraray) may be used.

In one embodiment, the water absorbing polymer is further characterized by its swelling ratio in water, whereas the swelling ratio is defined as the volume of the fully hydrated polymer, also called hydrogel, to that of the dry polymer. The swelling ratio is governed by the extent of cross-linking: the higher the cross-linking density, the lower the swelling ratio. In one embodiment, the swelling ratio does not exceed 100, in another embodiment does not exceed 75 and in yet another embodiment does not exceed 50. A convenient way to measure the maximum swelling ratio is to weigh the water absorbing polymer before and after having swollen it to its full extent with deionized water. The maximal swelling ratio is then given by dividing the weight of the fully swollen polymer (or hydrogel) by the weight of the dry polymer. The swelling ratio is usually defined at room temperature, for example 20° C.

In one embodiment, directed to high performance water-based fragrance emitters, characterized by fast room fragrance filling and high room fragrance intensity, the size of the fragrance emitter before swelling does not exceed about 4 mm diameter and the swelling ratio does not exceed about 100. In another embodiment, directed to high performance water-based fragrance emitters, characterized by fast room fragrance filling and high room fragrance intensity, the size of the fragrance emitter before swelling does not exceed about 2.5 mm diameter and the swelling ratio does not exceed about 50.

Fragrance Ingredient

In accordance with one embodiment, the plurality of water beads may also include a fragrance composition. In one embodiment, the fragrance composition may include at least one fragrance ingredient. In another embodiment, the fragrance composition may further comprise at least a second fragrance ingredient. In yet another embodiment, the fragrance composition may include a mixture of two or more fragrance ingredients.

The character of a fragrance (the so-called "hedonic character") relies on the contribution of all components of a fragrance through evaporation. Fragrances typically comprise one or more fragrance ingredients, often having different volatilities, boiling points and odor detection thresholds. Highly volatile fragrance components (so-called "Top Notes") are responsible for the initial impression of a fragrance. Less volatile fragrance components (so-called "Middle Notes", also known as "Heart Notes", and so-called "Bottom Notes", also known as "Base Notes") are responsible for the long-lasting impression of a fragrance. A fragrance's character depends on the harmonization of Top Note, Middle Note, and Bottom Note.

Fragrances play an important differentiating role for competitive products in the fast moving consumer goods sector. Nevertheless, the market dynamics in the air-freshener business are changing. Consumers of air freshening devices are no longer satisfied with their devices merely providing an odour eliminating or deodorizing effect, increasingly, they look to these products to provide a home signature and an expression of self. There is a need to provide perfume formulators with a wider palette of ingredients, which they can use to create differentiating olfactive impressions, while still providing emitting systems showing minimized and easily removable residues once the end of life of the emitting system has been reached, combined with a visual end of life signal. Fragrance ingredients that can provide typical base note olfactive impressions of softness, warmth, solidity and depth, and those particularly that are in the woody, chypre or musk olfactive direction, are increasingly sought after fragrance ingredients for use in air freshening devices in order to achieve differentiation in a competitive landscape.

In addressing the shortcomings in the art, air freshening devices of the present disclosure permit a higher evaporation rate of the Bottom Notes as compared to a passive system at room temperature. Consequently, when designing fragrance compositions for air freshening devices according to the present disclosure, perfumers no longer have to control the amount of Bottom Notes to prevent an evaporation profile that is too slow. The present air freshening device permits substantially the same ease of evaporation to all fragrance ingredients irrespective of their physicochemical properties such as volatility and thus leads to the balanced nature of the fragrance emitted from the device. Without wishing to be bound by any theory applicant believes that due to the combination of water beads and heat, the evaporation of bottom notes increases, along with the speed of diffusion or room filling, i.e. the time for a fragrance to fill a volume, as compared to passive systems.

The fragrance ingredients according to the present disclosure may be defined by their standard equilibrium headspace concentration ($HS_i^0$). The standard equilibrium headspace concentration ($HS_i^0$), expressed in microgram/liter (µg/L), refers to the concentration of the ingredient in equilibrium with the condensed form—that is solid or liquid form—of this ingredient at a temperature of 25° C. and under a pressure of 1 atmosphere. It can be measured by using any of the known quantitative headspace analysis techniques in the art. A suitable method is described in Mueller and Lamparsky in Perfumes: Art, Science and Technology, Chapter 6 "The Measurement of Odors" at pages 176-179 (Elsevier 1991).

In one example, $HS_i^0$ may be measured as follows: 500 mg of the test compound is added to a headspace container which is then sealed. The container is then incubated at constant 25° C. until the compound reaches equilibrium between the gas and the liquid phase. A defined volume of this saturated headspace (usually 0.5-1.0 liter) is trapped on a micro filter using Porapak Q as sorbent. After filter extraction with an appropriate solvent (usually 30-100 microliters methyl tertiary butyl ether), an aliquot of the extract is analyzed by GC. Quantification was performed by the external standard calibration method. The concentration in the original headspace can be calculated (in terms of µg/L) from the headspace volume sucked through the micro filter and the aliquot of the filter extract injected into the gas chromatograph. The final headspace concentration value of a given test compound is obtained as the mean value of three independent measurements each. Further information of the technique hereinabove described may be found in the article of Etzweiler, F.; Senn E, and Neuner-Jehle N., Ber. Bunsen-Ges. Phys. Chem. 1984, 88, 578-583.

For fragrance ingredients classified as Top Notes, the $HS_i^0$ may be greater than about 1000 µg/L. Suitable Top Note fragrance ingredients according to the present disclosure may be selected from hexyl acetate (hexyl acetate), acetophenone (acetophenone), hexan-1-ol (hexan-1-ol), hexanal (hexanal), heptanal (heptanal), nonanal (nonanal), aldehyde isononylic (3,5,5-trimethylhexanal), allyl caproate (allyl hexanoate), allyl oenanthate (allyl heptanoate), amyl butyrate (pentyl butyrate), amyl vinyl carbinol (oct-1-en-3-ol), Anapear ((E)-methyl octa-4,7-dienoate), benzaldehyde (benzaldehyde), benzyl formate (benzyl formate), benzyl methyl ether ((methoxymethyl)benzene), bornyl acetate ((2S,4S)-1,7,7-trimethyl-bicyclo[2.2.1]heptan-2-yl acetate), butyl acetate (butyl acetate), camphene ((1S,4R)-2,2-dimethyl-3-methylenebicyclo[2.2.1]heptane), Citronella (3,7-dimethyloct-6-enal), cresyl methyl ether para (1-methoxy-4-methylbenzene), Cyclal C (2,4-dimethylcyclohex-3-enecarbaldehyde), cymene para (p-cymene), trans-4-decenal ((E)-dec-4-enal), delta-3 carene ((1S,6S)-3,7,7-trimethylbicyclo[4.1.0]hept-3-ene), diethyl malonate (diethyl malonate), dihydro anethole (1-methoxy-4-propylbenzene), dihydro myrcenol (2,6-dimethyloct-7-en-2-ol), dimethyl octenone (4,7-dimethyloct-6-en-3-one), dimetol (2,6-dimethylheptan-2-ol), dimyrcetol (2,6-dimethyloct-7-en-2-yl formate), dipentene (1-methyl-4-(prop-1-en-2-yl)cyclohex-1-ene), estragole (1-allyl-4-methoxybenzene), ethyl acetate (ethyl acetate), ethyl acetoacetate (ethyl 3-oxobutanoate), ethyl amyl ketone (octan-3-one), ethyl benzoate (ethyl benzoate), ethyl butyrate (ethyl butyrate), ethyl caproate (ethyl hexanoate), ethyl isoamyl ketone (6-methylheptan-3-one), ethyl isobutyrate (ethyl 2-methylpropanoate), ethyl methyl-2-butyrate (ethyl 2-methylbutanoate), ethyl oenanthate (ethyl heptanoate), ethyl propionate (ethyl propanoate), eucalyptol ((1s,4s)-1,3,3-trimethyl-2-oxabicyclo[2.2.2]octane), fenchone alpha (1,3,3-trimethylbicyclo[2.2.1]heptan-2-one), fenchyl acetate ((2S)-1,3,3-trimethylbicyclo[2.2.1]heptan-2-yl acetate), fenchyl alcohol ((1S,2R,4R)-1,3,3-trimethylbicyclo[2.2.1]heptan-2-ol), Freskomenthe (2-(sec-butyl)cyclohexanone), geranodyle (2-(2-hydroxypropan-2-yl)-5-methylcyclohexanol), guaiacol (2-methoxyphenol), trans-2-hexenal (E-hex-2-enal), cis-3-hexenol ((Z)-hex-3-en-1-ol), cis-3-hexenyl acetate (cis-hex-3-enyl acetate), cis-3-hexenyl butyrate ((Z)-hex-3-en-1-yl butyrate), cis-3-hexenyl formate ((Z)-hex-3-en-1-yl formate), cis-3-hexenyl isobutyrate ((Z)-hex-3-en-1-yl isobutyrate), cis-3-hexenyl 2-methyl-butyrate ((Z)-hept-3-en-1-yl 2-methyl butanoate), cis-3-hexenyl propionate ((Z)-hex-3-en-1-yl propionate), hexyl butyrate (hexyl butyrate), hexyl isobutyrate (hexyl isobutyrate), hexyl propionate (hexyl propionate), hydratropic aldehyde (2-phenylpropanal), isoamyl propionate (isopentyl propionate), isobutyl isobutyrate (isobutyl isobutyrate), isocyclocitral (2,4,6-trimethylcyclohex-3-enecarbaldehyde), Isopentyrate (4-methylpent-4-en-2-yl isobutyrate), isopropyl 2-methyl butyrate (isopropyl 2-methyl butanoate), isopulegol (5-methyl-2-(prop-1-en-2-yl)cyclohexanol), Leaf acetal ((Z)-1-(1-ethoxyethoxy)hex-3-ene), Lime oxide (isomer mixture)limetol (2,2,6-trimethyl-6-vinyltetrahydro-2H-pyran), linalool oxide (2-(5-methyl-5-vinyltetrahydrofuran-2-yl)propan-2-ol), linalool (3,7-dimethylocta-1,6-dien-3-ol), Manzanate (ethyl 2-methylpentanoate), Melonal (2,6-dimethylhept-5-enal), menthone (2-isopropyl-5-methylcyclohexanone), methyl amyl ketone (heptan-2-one), methyl benzoate (methyl benzoate), Methyl camomile (butyl 2-methylpentanoate), methyl hexyl ketone (octan-2-one), Methyl pamplemousse (6,6-dimethoxy-2,5,5-trimethylhex-2-ene), methyl salicylate (methyl 2-hydroxybenzoate), nonanyl acetate (nonanyl acetate), ocimene ((E)-3,7-dimethylocta-1,3,6-triene), octenyl acetate (oct-1-en-3-yl acetate), Pandanol ((2-methoxyethyl)benzene), alpha-pinene (alpha-pinene), beta-pinene (beta-pinene), prenyl acetate (3-methylbut-2-en-1-yl acetate), gamma-terpinene (1-isopropyl-4-methylcyclohexa-1,4-diene), terpinolene (1-methyl-4-(propan-2-ylidene)cyclohex-1-ene), tetrahydro citral (3,7-dimethyloctanal), tetrahydro linalool (3,7-dimethyloctan-3-ol), tricyclal (2,4-dimethylcyclohex-3-enecarbaldehyde), gamma-valerolactone (5-methyldihydrofuran-2(3H)-one) and mixtures thereof.

The fragrance composition may comprise from about 0% to about 50%, in another embodiment from about 0% to about 35%, in yet another embodiment from about 0% to about 15%, or any individual number within the range, by weight of the fragrance composition of a Top Note fragrance ingredient.

For fragrance ingredients classified as Middle Notes, the $HS_i^0$ may be from about 100 µg/L to about 1000 µg/L. Suitable Middle Note fragrance ingredients may be selected from Acetal E ((2-(1-ethoxyethoxy)ethyl)benzene), Acetal R ((2-(1-propoxyethoxy)ethyl)benzene), acetanisole (1-(4-methoxyphenyl)ethanone), Adoxal (2,6,10-trimethylundec-9-enal), Agrumex (2-(tert-butyl)cyclohexyl acetate), alcohol C10 decylic (decan-1-ol), alcohol C12 dodecylic (dodecan-1-ol), alcohol C8 octylic (octan-1-ol), alcohol C9 nonylic (nonan-1-ol), aldehyde C 11 undecylenic (undec-10-enal), aldehyde C 110 undecylic (undecanal), aldehyde C 12 LAURIC (dodecanal), aldehyde C 12 MNA (2-methylundecanal), aldehyde iso C 11 ((E)-undec-9-enal), allyl amyl glycolate (allyl 2-(isopentyloxy)acetate), allyl cyclohexyl propionate (allyl 3-cyclohexylpropanoate), Ambrinol (2,5,5-trimethyl-1,2,3,4,4a,5,6,7-octahydronaphthalen-2-ol), amyl benzoate (pentyl benzoate), amyl caproate (pentyl hexanoare), amyl cinnamic aldehyde ((Z)-2-benzylideneheptanal), amyl phenyl acetate (pentyl 2-phenylacetate), amyl salicylate (pentyl 2-hydroxybenzoate), anethole synthetic ((E)-1-methoxy-4-(prop-1-en-1-yl)benzene), anisyl acetate (4-methoxybenzyl acetate), anisyl alcohol ((4-methoxyphenyl)methanol), Anther ((2-(isopentyloxy)ethyl)benzene), Aubepine para cresol (4-methoxybenzaldehyde), benzyl acetone (4-phenylbutan-2-one), benzyl butyrate (benzyl butyrate), enzyl isobutyrate (benzyl isobutyrate), benzyl isovalerate (benzyl 3-methylbutanoate), benzyl propionate (benzyl propionate), Bergamyl acetate (2-methyl-6-methyleneoct-7-en-2-yl acetate) Berryflor (ethyl 6-acetoxyhexanoate), Boisiris ((1S,2R,5R)-2-ethoxy-2,6,6-trimethyl-9-methylenebicyclo[3.3.1]nonane), butyl butyro lactate (1-butoxy-1-oxopropan-2-yl butyrate), butyl cyclohexanol para (4-(tert-butyl)cyclohexanol), butyl cyclohexyl acetate para (4-(tert-butyl)cyclohexyl acetate), butyl quinoline secondary (6-(sec-butyl)quinoline), carvone laevo (2-methyl-5-(prop-1-en-2-yl)cyclohex-2-enone), caryophyllene ((Z)-4,11,11-trimethyl-8-methylenebicyclo[7.2.0]undec-4-ene), Cashmeran (1,1,2,3,3-pentamethyl-2,3,6,7-tetrahydro-1H-inden-4(5H)-one), cedrene epoxide ((1aS,2aR,3R,5aS,7R,7aR)-octahydro-3,6,6,7a-tetramethyl-2H-2a,7-methanozuleno 5,6-b oxirene), cedroxyde ((4Z,8Z)-1,5,9-trimethyl-13-oxabicyclo[10.1.0]trideca-4,8-diene), cedryl methyl ether ((1R,6S,8aS)-6-methoxy-1,4,4,6-tetramethyloctahydro-1H-5,8a-methanoazulene), Celery ketone (3-methyl-5-propylcyclohex-2-enone), Centifolyl (phenethyl pivalate), Cetonal (2-methyl-4-(2,6,6-trimethylcyclohex-2-en-1-yl)butanal), Cetone alpha ((E)-3-methyl-4-(2,6,6-trimethylcyclohex-2-en-1-yl)but-3-en-2-one), cinnamic aldehyde (cinnamaldehyde), cinnamyl acetate (cinnamyl acetate), Citral dimethyl acetal ((E)-1,1-dimethoxy-3,7-dimethylocta-2,6-diene), Citrodyle (acetylated eucalyptol oil), citronellol (3,7-dimethyloct-6-en-1-ol), citronellyl acetate (3,7-dimethyloct-6-en-1-yl acetate), citronellyl butyrate (3,7-dimethyloct-6-en-1-yl butanoate), citronellyl formate (3,7-dimethyloct-6-en-1-yl formate), citronellyl isobutyrate (3,7-dimethyloct-6-en-1-yl isobutyrate), citronellyl nitrile (3,7-dimethyloct-6-enenitrile), citronellyl oxyacetaldehyde (2-((3,7-dimethyloct-6-en-1-yl)oxy)acetaldehyde), citronellyl propionate (3,7-dimethyloct-6-en-1-yl propionate), Clonal (dodecanenitrile), Coniferan (2-(tert-pentyl)cyclohexyl acetate), creosol (2-methoxy-4-methylphenol), cresyl acetate para (p-tolyl acetate), cresyl isobutyrate para (p-tolyl isobutyrate), Cumin nitrile (4-isopropylbenzonitrile), Cuminic aldehyde (4-isopropylbenzaldehyde), Cuminyl alcohol ((4-isopropylphenyl)methanol). Cyclamen aldehyde extra (3-(4-isopropylphenyl)-2-methylpropanal), Cyclogalbanate (allyl 2-(cyclohexyloxy)acetate), cyclohexyl ethyl acetate (2-cyclohexylethyl acetate), cyclohexyl salicylate (cyclohexyl 2-hydroxybenzoate), cyclomethylene citronellol (3-(4-methylcyclohex-3-en-1-yl)butan-1-ol), Cyperate (3-tert-butyl-cyclohexyl acetate), Damascenone ((E)-1-(2,6,6-trimethylcyclohexa-1,3-dien-1-yl)but-2-en-1-one), decahydro naphtyl formate beta (1,2,3,4,4a,5,6,7,8,8a-decahydronaphthalen-2-ylformate), decalactone delta(6-pentyltetrahydro-2H-pyran-2-one), decalactone gamma (5-hexyldihydrofuran-2(3H)-one), Decatone (6-isopropyloctahydronaphthalen-2(1H)-one), decyl methyl ether (methoxy-decane), delphone (2-pentylcyclopentanone), dihexyl fumarate (dihexyl-but-2-enedioate), dihydro ambrate (2-(sec-butyl)-1-vinylcyclohexyl acetate), dihydro cyclacet ((3aa,4a,5a,7a,7aa)-octahydro-4,7-methano-1H-inden-5-yl acetate), dihydro eugenol (2-methoxy-4-propylphenol), dihydro farnesal ((Z)-3,7,11-trimethyldodeca-6,10-dienal), dihydro ionone beta (4-(2,6,6-trimethylcyclohex-1-en-1-yl)butan-2-one), dihydro jasmone (3-methy-2-pentylcyclopent-2-enone), dihydro linalool (3,7-dimethyloct-6-en-3-ol), dihydro terpineol (2-(4-methylcyclohexyl)propan-2-ol), dimethyl anthranilate (methyl 2-(methylamino)benzoate), dimethyl benzyl carbinol (2-methyl-1-phenylpropan-2-ol), dimethyl benzyl carbinyl acetate (2-methyl-1-phenylpropan-2-yl acetate), dimethyl benzyl carbinyl butyrate (2-methyl-1-phenylpropan-2-yl butyrate), dimethyl phenyl ethyl carbinol (2-methyl-4-phenylbutan-2-ol), dimethyl phenyl ethyl carbinyl acetate (2-methyl-4-phenylbutan-2-yl acetate), diphenyl methane (diphenylmethane), diphenyl oxide (oxydibenzene), Dupical ((E)-4-((3aS,7aS)-hexahydro-1H-4,7-methanoinden-5(6H)-ylidene)butanal), Ebanol ((E)-3-methyl-5-(2,2,3-trimethylcyclopent-3-en-1-yl)pent-4-en-2-ol), ethyl caprylate (ethyl octanoate), ethyl cinnamate (ethyl cinnamate), ethyl decadienoate ((2E,4Z)-ethyl deca-2,4-dienoate), ethyl linalool ((E)-3,7-dimethylnona-1,6-dien-3-ol), ethyl linalyl acetate ((Z)-3,7-dimethylnona-1,6-dien-3-yl acetate), ethyl octenoate-2 (ethyl oct-2-enoate), ethyl pelargonate (ethyl nonanoate), ethyl phenoxy acetate (2-(phenoxy)eth-2-yl acetate), ethyl phenyl acetate (ethyl 2-phenylacetate), ethyl phenyl glycidate (ethyl 3-phenyloxirane-2-carboxylate), ethyl salicylate (ethyl 2-hydroxybenzoate), eugenol (4-ally-2-methoxyphenol), eugenyl acetate (4-allyl-2-methoxyphenyl acetate), farnesene ((E)-7,11-dimethyl-3-methylenedodeca-1,6,10-triene), Fennaldehyde (3-(4-methoxyphenyl)-2-methylpropanal), Fixambrene (3a,6,6,9a-tetramethyldodecahydronaphtho[2,1-b]furan), Floralozone (3-(4-ethylphenyl)-2,2-dimethylpropanal), Floramat (2-(tert-butyl)cyclohexyl ethyl carbonate), Florol (2-isobutyl-4-methyltetrahydro-2H-pyran-4-ol), Floropal (2,4,6-trimethyl-4-phenyl-1,3-dioxane), Florhydral (3-(3-isopropylphenyl)butanal), Folenox (4,4,8,8-tetramethyloctahydro-4a,7-methanonaphtho[1,8a-b]oxirene), Folione (methyl oct-2-ynoate), Folrosia (4-isopropylcyclohexanol), Fraistone (ethyl 2-(2,4-dimethyl-1,3-dioxolan-2-yl)acetate), Fructone (ethyl 2-(2-methyl-1,3-dioxolan-2-yl)acetate), Fruitate ((3aS,4S,7R,7aS)-ethyl octahydro-1H-4,7-methanoindene-3a-carboxylate). Gardenol (1-phenylethyl acetate). Gardocyclene ((3aR,6S,7aS)-3a,4,5,6,7,7a-hexahydro-1H-4,7-methanoinden-6-yl isobutyrate), Georgywood (1-(1,2,8,8-tetramethyl-1,2,3,4,5,6,7,8-octahydronaphthalen-2-yl) ethanone), Geraniol ((E)-3,7-dimethylocta-2,6-dien-1-ol), Geranitrile (3,7-dimethyl-octa-2,6-dienenitrile). Geranyl acetate ((E)-3,7-dimethylocta-2,6-dien-1-yl acetate), Geranyl acetone ((E)-6,10-dimethylundeca-5,9-dien-2-one), Geranyl butyrate ((E)-3,7-dimethylocta-2,6-dien-1-yl butanoate), Geranyl crotonate ((E)-3,7-dimethylocta-2,6-dien-1-yl but-2-enoate), Geranyl formate ((E)-3,7-dimethylocta-2,6-dien-1-yl formate), Geranyl isobutyrate ((E)-3,7-dimethylocta-2,6-dien-1-yl isobutyrate), Geranyl propionate ((E)-3,7-dimethylocta-2,6-dien-1-yl propionate), Givescone (ethyl 2-ethyl-6,6-dimethylcyclohex-2-enecarboxylate), Glycolierral (2-(8-isopropyl-6-methylbicyclo[2.2.2]oct-5-en-2-yl)-1,3-dioxolane), Guaiyl acetate (2-(3,8-dimethyl-1,2,3,4,5,6,7,8-octahydroazulen-5-yl)propan-2-yl acetate), Gyrane (2-butyl-4,6-dimethyl-3,6-dihydro-2H-pyran), Heliotropine crystals (benzo[d][1,3]dioxole-5-carbaldehyde), cis-3-hexenyl benzoate ((Z)-hex-3-en-1-yl benzoate), cis-3-hexenyl hexenoate ((Z)—(Z)-hex-3-en-1-yl hex-3-enoate), cis-3-hexenyl salicylate ((Z)-hex-3-en-1-yl 2-hydroxybenzoate), cis-3-hexenyl tiglate ((E)-(Z)-hex-3-en-1-yl 2-methylbut-2-enoate), hexyl benzoate (hexyl benzoate), hydroxycitronellal dimethyl acetal (8,8-dimethoxy-2,6-dimethyloctan-2-ol), Indoflor (4,4a,5,9b-tetrahydroindeno[1,2-d][1,3]dioxine), indole pure (H-indole), indolene (8,8-di(1H-indol-3-yl)-2,6-dimethyloctan-2-ol), ionone beta ((E)-4-(2,6,6-trimethylcyclohex-1-en-1-yl)but-3-en-2-one), irisantheme ((E)-3-methyl-4-(2,6,6-trimethylcyclohex-2-en-1-yl)but-3-en-2-one), Irisone alpha ((E)-4-(2,6,6-trimethylcyclohex-2-en-1-yl)but-3-en-2-one), Ironal ((E)-4-(2,5,6,6-tetramethyl-1-cyclohex-2-enyl)but-3-en-2-one), Irone alpha ((E)-4-(2,5,6,6-tetramethylcyclohex-2-en-1-yl)but-3-en-2-one), Irone F ((E)-4-(2,5,6,6-tetramethylcyclohex-2-en-1-yl)but-3-en-2-one), Iso E super (1-(2,3,8,8-tetramethyl-1,2,3,4,5,6,7,8-octahydronaphthalen-2-yl)ethanone), isobornyl propionate ((1S)-1,7,7-trimethylbicyclo[2.2.]heptan-2-yl propanoate), isobutyl benzoate (isobutyl benzoate), isobutyl phenyl acetate (isobutyl 2-phenylacetate), isobutyl quinoline-2 (2-isobutylquinoline), isobutyl salicylate (isobutyl 2-hydroxybenzoate), isocaryol acetate ((2-methoxy-4-prop-1-enylphenyl) acetate), isoeugenol ((E)-2-methoxy-4-(prop-1-en-1-yl)phenol), Jasmal (3-pentyltetrahydro-2H-pyran-4-yl acetate), Jasmin lactone delta ((Z)-6-(pent-2-en-1-yl) tetrahydro-2H-pyran-2-one), Jasmin lactone gamma ((Z)-5-(hex-3-en-1-yl)-5-methyldihydrofuran-2(3H)-one), Jasmolactone ((E)-6-(pent-3-en-1-yl)tetrahydro-2H-pyran-2-one). Jasmone cis ((Z)-3-methyl-2-(pent-2-en-1-yl)cyclopent-2-enone), Jasmonyl (3-butyl-5-methyltetrahydro-2H-pyran-4-yl acetate), Kephalis (4-(1-ethoxyvinyl)-3,3,5,5-tetramethylcyclohexanone), Kohinool (3,4,5,6,6-pentamethylheptan-2-ol), Labienone ((E)-2,4,4,7-tetramethylnona-6,8-dien-3-one), Lactoscatone (2,8,8-trimethyloctahydro-1H-4a,2-(epoxymethano)naphthalen-O-one), Citral lemarome N ((E)-3,7-dimethylocta-2,6-dienal), Lemonile ((2E,6Z)-3,7-dimethylnona-2,6-dienenitrile), Lierral (8-isopropyl-6-methyl-bicyclo[2.2.2]oct-5-ene-2-carbaldehyde), Lilial (3-(4-(tert-butyl)phenyl)-2-methylpropanal), linalyl acetate (3,7-dimethylocta-,6-dien-3-yl acetate), linalyl butyrate (3,7-dimethylocta-1,6-dien-3-yl butanoate), linalyl formate (3,7-dimethylocta-1,6-dien-3-yl formate), linalyl isobutyrate (3,7-dimethylocta-1,6-dien-3-yl isobutyrate), linalyl propionate (3,7-dimethylocta-1,6-dien-3-yl propionate). Lindenol (2-(4-methylcyclohex-3-en-1-yl)propan-2-ol), Majantol (2,2-dimethyl-3-(m-tolyl)propan-1-ol), Mayol ((4-isopropylcyclohexyl)methanol), menthanyl acetate (2-(4-methylcyclohexyl)propan-2-yl acetate), Metambrate (2-(sec-butyl)-1-methylcyclohexyl acetate), methoxy phenyl butanone (4-(4-methoxyphenyl)butan-2-one), methyl acetophenone (1-(p-tolyl)ethanone), methyl cinnamate (methyl cinnamate), methyl cinnamic aldehyde ((Z)-2-methyl-3-phenylacryladehyde), methyl decalactone gamma (5-hexyl-5-methyldihydrofuran-2(3H)-one), methyl diantilis (2-ethoxy-4-(methoxymethyl)phenol), methyl diphenyl ether (2-methoxy-1,1'-biphenyl), methyl ional alpha ((Z)-2-methyl-4-(2,6,6-trimethyl-1-cyclohex-2-enyl)but-3-enal), methyl isoeugenol ((E)-1,2-dimethoxy-4-(prop-1-en-1-yl)benzene), methyl octalactone (5-butyl-4-methyl-dihydro-2(3H)-furanone), methyl octyl acetaldehyde (2-methyl-decanal), methyl octyne carbonate (methyl non-2-ynoate), methyl phenyl acetate (methyl 2-phenylacetate), methyl quinoline para (6-methylquinoline), Moxalone (1a,3,3,4,6,6-hexamethyl-a,2,3,4,5,6,7,7a-octahydronaphtho[2,3-b]oxirene), Myraldene (4-(4-methylpent-3-en-1-yl)cyclohex-3-enecarbaldehyde), Neofolione ((E)-methyl non-2-enoate), Nerol C (3,7-dimethyl-2,6-octadien-1-ol), neryl acetate ((Z)-3,7-dimethylocta-2,6-dien-1-yl acetate), Nonadyl (6,8-dimethylnonan-2-ol), nopyl acetate (2,4,6,6-dimethylbicyclo[3.1.1]hept-2-en-2-yl)ethyl acetate), octahydro coumarin (octahydro-benzopyran-2one), octalactone delta (6-propyltetrahydro-2H-pyran-2-one), octalactone gamma (5-butyldihydrofuran-2(3H)-one), Orcinyl 3 (3-methoxy-5-methylphenol), orivone (4-(tert-pentyl)cyclohexanone), osvrol (7-methoxy-3,7-dimethyloctan-2-ol), oxyoctaline formate (2,4a,5,8a-tetramethyl-1,2,3,4,4a,7,8,8a-octahydronaphthalen-1-yl formate), Parmavert (1,1-dimethoxynon-2-yne), Peach pure (5-heptyldihydrofuran-2(3H)-one), pelargol (3,7-dimethyloctan-1-ol), phenoxanol (3-methyl-5-phenylpentan-1-ol), phenoxy ethyl alcohol (2-phenoxyethanol), phenoxy ethyl isobutrate (2-(phenoxy)ethyl 2-methylpropanoate), phenoxy ethyl isobuyrate (2-(phenoxy)ethyl 2-methylpropanoate), phenyl ethyl acetate (phenethyl acetate), phenyl ethyl alcohol (2-phenylethanol), phenyl ethyl butyrate (phenethyl butanoate), phenyl ethyl formate (phenethyl formate), phenyl ethyl isobutyrate (phenethyl isobutyrate), phenyl propionic aldehyde (3-phenylpropanal), phenyl propyl acetate (3-phenylpropyl acetate), phenyl propyl alcohol (3-phenylpropan-1-ol), Pinoacetaldehyde (3-(6,6-dimethylbicyclo[3.1.1]hept-2-en-2-yl)propanal), Plicatone ((4aS,8aR)-7-methyloctahydro-1,4-methanonaphthalen-6(2H)-one), Precarone ((1S,4R,6S)-4,7,7-trimethyl-4-(3-methylbut-2-en-1-yl)bicyclo[4.1.0]heptan-3-one), Prunolide (5-pentyldihydrofuran-2(3H)-one), Pyralone (6-(sec-butyl)quinoline), Radjanol ((E)-2-ethyl-4-(2,2,3-trimethylcyclopent-3-en-1-yl)but-2-en-1-ol), Resedal (2-benzyl-4,4,6-trimethyl-1,3-dioxane), Rhodinyl acetate (3,7-dimethyloct-6-en-1-yl acetate), Rhubafuran (2,4-dimethyl-4-phenyltetrahydrofuran), Rhubofix ((2R,8aS)-3',6-dimethyl-3,4,4a,5,8,8a-hexahydro-1H-spiro[1,4-methanonaphthalene-2,2'-oxirane]), Rhuboflor ((4aR,8aS,E)-6-ethylideneoctahydro-2H-5,8-methanochromene), Rosalva (dec-9-en-1-ol), Sandalore (3-methyl-5-(2,2,3-trimethylcyclopent-3-en-1-yl)pentan-2-ol), Scentenal ((3aR,4R,6S,7R,7aR)-6-methoxyoctahydro-1H-4,7-methanoindene-1-carbaldehyde), skatole (3-methyl-1H-indole), Spirambrene (2',2',3,7,7-pentamethylspiro[bicyclo[4.1.0]heptane-2,5'-[1,3]dioxane]), Stemone ((E)-5-methylheptan-3-one oxime), Strawberry pure (ethyl methyl phenyl glycidate), Styrallyl propionate (1-phenylethyl propionate), Syringa aldehyde (2-(p-tolyl)acetaldehyde), Tangerinol ((E)-6,10-dimethylundeca-5,9-dien-2-yl acetate), terpinene alpha (1-methyl-4-propan-2-ylcyclohexa-1,3-diene), terpinyl acetate (2-(4-methylcyclohex-3-en-1-yl)propan-2-yl acetate), Terranil (3-(2,6,6-trimethyl-1-cyclohexen-1-yl)-prop-2-enenitrile), tetrahydro linalyl acetate (3,7-dimethyloctan-3-yl acetate), tetrahydro myrcenol (2,6-dimethyloctan-2-ol), tridecenonitrile ((E)-tridec-2-enenitrile), Tropional (3-(benzo[d][1,3]dioxol-5-yl)-2-methylpropanal), undecatriene ((3E,5Z)-undeca-1,3,5-triene), undecavertol ((E)-4-methyldec-3-en-5-ol), Veloutone (2,2,5-trimethyl-5-pentylcyclopentanone), Verdol (2-(tert-butyl)cyclohexanol), Verdyl acetate ((3aR6S,7aS)-3a,4,5,6,7,7a-hexahydro-1H-4,7-methanoinden-6-yl acetate), Verdyl propionate ((3aR,6S,7aS)-3a,4,5,6,7,7a-hexahydro-1H-4,7-methanoinden-6-yl propionate), Vemaldehyde (1-methyl-4-(4-methylpentyl)cyclohex-3-enecarbaldehyde), Vetynal ((2R,5R,8S)-4,4,8-trimethyltricyclo[6.3.1.02,5]dodecan-1-yl acetate), Vetyvenal ([(3Z)-4,11,11-trimethyl-8-methylidene-5-bicyclo[7.2.0]undec-3-enyl] acetate), Viridine ((2,2-dimethoxyethyl)benzene), 3-(4-isobutyl-2-methylphenyl)propanal and mixtures thereof.

The fragrance composition may comprise from about 30% to about 97%, in another embodiment from about 60% to about 95%, in yet another embodiment from about 65% to about 90%, or any individual number within the range, by weight of the fragrance composition of a Middle Note fragrance ingredient.

For fragrance ingredients classified as Bottom Notes, the $HS_i^0$ may be less than about 100 µg/L. Suitable Bottom Note fragrance ingredients according to the present disclosure may be selected from Acetal CD ((2-benzyl-1,3-dioxolan-4-yl)methanol), Aldrone (2-methyl-4-(5,6,6-trimethylbicyclo[2.2.1]hept-2-yl-cyclohexanone), Ambroxan (3a,6,6,9a-tetramethyldodecahydronaphtho[2,1-b]furan), Benzophenone (benzophenone), Benzyl Benzoate (decan-1-ol), Benzyl Cinnamate (dodecan-1-ol), Benzyl Phenyl Acetate (octan-1-ol), Cepionate (nonan-1-ol), Cetalox (3a,6,6,9a-tetramethyldodecahydronaphtho[2,1-b]furan), Citronellyl Ethoxalate (3,7-dimethyloct-6-en-1-yl ethyl oxalate), Cresyl Caprylate Para (p-toyl octanoate), Cresyl Phenyl Acetate Para (p-tolyl 2-phenylacetate), Cyclohexal (4-(4-hydroxy-4-methylpentyl)cyclohex-3-enecarbaldehyde), Diethyl Phthalate (diethyl phthalate), Dione (2-(2-(3,3,5-trimethylcyclohexyl)acetyl)cyclopentanone), Dodecalactone Delta (6-heptyltetrahydro-2H-pyran-2-one), Dodecalactone Gamma (5-octyldihydrofuran-2(3H)-one), Ethyl Maltol (2-ethyl-3-hydroxy-4H-pyran-4-one), Ethyl Vanillin (3-ethoxy-4-hydroxybenzaldehyde), Eugenyl Phenyl Acetate (2-methoxy-4-(2-propenyl)phenyl 2-phenyl acetate), Evernyl (methyl 2,4-dihydroxy-3,6-dimethylbenzoate), Fixolide (1-(3,5,5,6,8,8-hexamethyl-5,6,7,8-tetrahydronaphthalen-2-yl)ethanone), Geranyl Phenyl Acetate ((E)-3,7-dimethylocta-2,6-dien-1-yl 2-phenylacetate), Geranyl Tiglate ((E)-(E)-3,7-dimethylocta-2,6-dien-1-yl 2-methylbut-2-enoate), Grisalva (3a-ethyl-6,6,9a-trimethyldodecahydronaphtho[1,2-c]furan), Hedione (methyl 2-(3-oxo-2-pentylcyclopentyl)acetate), Hexyl Cinnamic Aldehyde ((E)-2-benzylideneoctanal), Hexyl Salicylate (hexyl 2-hydroxybenzoate), Methyl Cedryl Ketone (1-(1S,8aS)-1,4,4,6-tetramethyl-2,3,3a,4,5,8-hexahydro-1H-5,8a-methanoazulen-7-yl)ethanone), Laitone (8-isopropyl-1-oxaspiro[4.5]decan-2-one), Linalyl Benzoate (3,7-dimethylocta-1,6-dien-3-yl benzoate), Linalyl Cinnamate (3,7-dimethylocta-1,6-dien-3-yl cinnamate), Linalyl Phenyl Acetate (3,7-dimethylocta-1,6-dien-3-yl 2-phenyl-acetate), Maltol (3-hydroxy-2-methyl-4H-pyran-4-one), Maltyl Isobutyrate (2-methyl-4-oxo-4H-pyran-3-yl isobutyrate), Methyl Cedryl Ketone (1-((1S,8aS)-1,4,4,6-tetramethyl-2,3,3a,4,5,8-hexahydro-1H-5,8a-methanoazulen-7-yl)ethanone), Methyl Dihydro Isojasmonate (methyl 2-hexyl-3-oxocyclopentanecarboxylate). Muscone (3-methylcyclopentadecanone), Myraldyl acetate ((4-(4-methylpent-3-en-1-yl)cyclohex-3-en-1-yl)methyl acetate), Nectaryl (2-(2-(4-methylcyclohex-3-en-1-yl)propyl)cyclopentanone), Okoumal (2,4-dimethyl-2-(5,5,8,8-tetramethyl-5,6,7,8-tetrahydronaphthalen-2-yl)-1,3-dioxolane), Oranile (tetradecanenitrile), Peonile (2-cyclohexylidene-2-phenylacetonitrile), Phenyl Ethyl Benzoate (2-phenethyl benzoate), Phenyl Ethyl Cinnamate (2-phenethyl cinnamate), Phenyl Ethyl Phenyl Acetate (2-phenethyl 2-phenylacetate), Propyl Diantilis (2-ethoxy-4-(isopropoxymethyl)phenol), Rosacetol (2,2,2-trichloro-1-phenylethyl acetate), Rosaphen (2-methyl-5-phenylpentan-1-ol), Sandela (3-((1R,2S,4R,6R)-5,5,6-trimethylbicyclo[2.2.1]heptan-2-yl)cyclohexanol), Timberol (1-(2,2,6-trimethylcyclohexyl)hexan-3-ol), Undecalactone Delta (6-hexyltetrahydro-2H-pyran-2-one), Vanillin (4-hydroxy-3-methoxybenzaldehyde), Vanitrope ((E)-2-ethoxy-5-(prop-1-en-1-yl)phenol), (E)-9-hydroxy-5,9-dimethyldec-4-enal and mixtures thereof.

Additional Bottom Note fragrance ingredients according to the present disclosure may be selected from Acetyl Iso Eugenol ((E)-2-methoxy-4-(prop-1-en-1-yl)phenyl acetate), Acetyl Vanillin (4-formyl-2-methoxyphenyl acetate), Amber Core (1-((2-(tert-butyl)cyclohexyl)oxy)butan-2-ol), Amberketal, Ambermax (3,8,8,11a-tetramethyldodecahydro-1H-3,5a-epoxynaphtho[2,1-c]oxepine), Ambrocenide ((2,4a,5,8a-tetramethyl-1,2,3,4,7,8-hexahydronaphthalen-1-yl) formate), Ambrofix ((4aR,5R,7aS,9R)-octahydro-2,2,5,8,8,9a-hexamethyl-4h-4a,9-methanoazuleno(5,6-d)-1,3-dioxole), Ambrox (3a,6,6,9a-tetramethyldodecahydronaphtho[2,1-b]furan), Ambroxan (3a,6,6,9a-tetramethyldodecahydronaphtho[2,1-b]furan), Azurone (((1S,8aR)-1,4,4-trimethyl-2,3,3a,4,5,8-hexahydro-1H-5,8a-methanoazulen-6-yl)methanol), Calone (7-isopentyl-2H-benzo[b][1,4]dioxepin-3(4H)-one), Cedrol (4-(1,3-benzodioxol-5-yl)butan-2-one), Cedryl acetate((1S,6R,8aR)-1,4,4,6-tetramethyloctahydro-1H-5,8a-methanoazulen-6-ol), Cetalox ((1S,6R,8aR)-1,4,4,6-tetramethyloctahydro-1H-5,8a-methanoazulen-6-ylacetate), Cinnamicacid (methyl 2,4-dihydroxy-3-methylbenzoate), Cinnamyl Cinnymate (3-phenylprop-2-enoic acid), Corylone (2-hydroxy-3-methylcyclopent-2-enone), Coumarin (2H-chromen-2-one), Cresyl ohenyl acetate (p-tolyl 2-phenylacetate), Cynnamyl Cinnamate (3-phenylprop-2-enyl 3-phenylprop-2-enoate), Ethyl Maltol (2-ethyl-3-hydroxy-4H-pyran-4-one), Ethyl Vanillin (3-ethoxy-4-hydroxybenzaldehyde), Evernyl (methyl 2,4-dihydroxy-3,6-dimethylbenzoate), Homofuronol (2-ethyl-4-hydroxy-5-methylfuran-3(2H)-one), Indole (1H-indole), Maltol (3-hydroxy-2-methyl-4H-pyran-4-one), Methyl Cinnamate (hexyl (E)-3-phenylprop-2-enoate), Mystikal (2-methylundecanoic acid), Neroline (2-ethoxynaphthalene), Oranger Crystal (1-naphthalen-2-ylethanone), Orcinyl-3 (3-methoxy-5-methylphenol), Para Cresyl Phenyl Acetate (Benzeneacetonitrile, alpha-cyclohexylidene-2-methyl-), Petalia (2-cyclohexylidene-2-phenylacetonitrile), Phenyl Acetic Acid (2-phenylacetic acid), Henyl Ethyl Cinnamate (phenyl-(E)-3-phenylprop-2-enoate), Phenyl Ethyl Salicyclate (phenethyl 2-hydroxybenzoate), Yara yara (2-methoxynaphthalene) and mixtures thereof.

An important class of Bottom Notes that can be exploited more fully in the air freshening device according to the present disclosure in the class of musk ingredients. Musks are highly valued molecules in perfumery and yet, they are under-utilized in water-based air freshening applications due to their low volatilities. Suitable musk bottom notes according to the present disclosure include those selected from the group consisting of Cashmeran (1,1,2,3,3-pentamethyl-2,3,6,7-tetrahydro-1H-inden-4(5H)-one), Galaxolide (4,6,6,7,8,8-hexamethyl-1,3,4,6,7,8-hexahydrocyclopenta[g]isochromene), Moxalone (1a,3,3,4,6,6-hexamethyl-1a,2,3,4,5,6,7,7a-octahydronaphtho[2,3-b]oxirene), Cosmone ((Z)-3-methylcyclotetradec-5-enone), Thibetolide (oxacyclohexadecan-2-one), Velvione ((Z)-cyclohexadec-5-enone), Muscenone ((Z)-3-methylcyclopentadec-5-enone), Nirvanolide ((E)-13-methyloxacyclopentadec-10-en-2-one), Habanolide ((E)-oxacyclohexadec-12-en-2-one), Civettone ((Z)-cycloheptadec-9-enone), musk C14 (1,4-dioxacyclohexadecane-5,16-dione), Ethylene brassylate (1,4-dioxacycloheptadecane-5,17-dione), Ambrettolide ((Z)-oxacycloheptadec-10-en-2-one), Serenolide (2-(1-(3,3-dimethylcyclohexyl)ethoxy)-2-methylpropyl cyclopropanecarboxylate), Sylkolide ((E)-2-((3,5-dimethylhex-3-en-2-yl)oxy)-2-methylpropyl cyclopropanecarboxylate), Silvanone, Musk CPD (cyclopentadecanone), Hexadecanolide (1-oxacycloheptadecan-2-one) and mixtures thereof.

The fragrance composition may comprise from about 3% to about 70%, in another embodiment from about 5% to about 50%, in yet another embodiment from about 10% to about 35%, or any individual number within the range, by weight of the fragrance composition of a Bottom Note fragrance ingredient.

Optional Ingredients

The fragrance emitter may also include other optional ingredients for particular applications. In one embodiment, the optional ingredients include, but are not limited to surfactants, water-soluble co-solvents, and water-insoluble or partially soluble co-solvents, which are essentially used for improving the solubility of fragrance ingredients in in the water phase, preservatives, and deodorizing agents.

In one embodiment, suitable surfactants include, but are not limited to, PEG 40 hydrogenated castor oil (Cremophor® RH 40 or Eumulgin® CO 40, commercially available from BASF), other types of the Cremophor® RH series or Eumulgin® CO series, and PEG 400 (Lipoxol®, commercially available from Sasol Olefins and Surfactants GmbH); C4-C18 alkyl ethoxylates with about 1-22 ethylene oxide units, TERGITOL, commercially available from The Dow Chemical Corporation, such as TERGITOL 15-S-9 (the condensation product of C11-C15 linear secondary alcohol with 9 moles ethylene oxide), and TERGITOL 24-L-6 NMW (the condensation product of C12-C14 primary alcohol with 6 moles ethylene oxide with a narrow molecular weight distribution); Neodol® commercially available from Shell Chemical Company, for example, Neodol® 45-9 (the condensation product of C14-C15 linear alcohol with 9 moles of ethylene oxide), Neodol® 23-6.5 (the condensation product of C12-C13 linear alcohol with 6.5 moles of ethylene oxide), Neodol® 45-7 (the condensation product of C14-C15 linear alcohol with 7 moles of ethylene oxide), and Neodol® 45-4 (the condensation product of C14-C15 linear alcohol with 4 moles of ethylene oxide), Neodol® 91-8; Kyro® EOB (the condensation product of C13-C15 alcohol with 9 moles ethylene oxide), commercially available from The Procter & Gamble Company; Cosmacol® NI19 (the mixture of linear and mono branched C12-C13 with 9 moles of ethylene oxide), commercially available from Sasol Olefins and Surfactants GmbH; Dehydol® series commercially available from Cognis/BASF, for example C8 to C18 (e.g. CO) with 2 to 14 moles of ethylene oxide, and mixtures thereof; TRIDECETH series, the condensation products of C13 alcohols and 2-21 moles of ethylene oxide, for example, TRIDECETH-9 and TRIDECETH-10, Dobanol® 91-8 commercially available from Shell Chemical Co., and Genapol® UD-080 commercially available from Clariant; mixed ethoxylates/propoxylates, such as Pluronic® surfactants, commercially available from BASF, Eumulgin® L commercially available from Cognis/BASF (e.g. PPG-1-PEG-9 lauryl glycol ether); condensation products of ethylene oxide (EO) with the product resulting from the reaction of propylene oxide and ethylene diamine.

In another embodiment, examples of non-ionic surfactants include certain of the commercially available Tetronic® compounds, commercially available from BASF; alkyl dialkyl amine oxides, such as C10-C18 alkyl dimethyl amine oxides and C8-C12 alkoxy ethyl dihydroxy ethyl amine oxides; alkyl polyglycosides; alkanoyl glucose amides, glycol sorbitol ethers containing 3-30 EO units (including, for example, sorbitol esters with oleic, myristic, stearic, palmitic acid, and the like), also known under the tradename TWEEN, such as TWEEN 20, TWEEN 40, and TWEEN 60; alkyl polyglycosides including, for example, C8-C10 polyglycosides (e.g. Radia® Easysurf 6881, commercially available from Oleon; ORAMIX CG110, commercially available from Seppic), C12-C16 alkyl polyglycosides (e.g. Plantaren®1200 NP, commercially available from Cognis/BASF), C8-C16 alkyl polyglycosides (e.g. Plantaren® 2000 commercially available from Cognis/BASF), C5 Amyl xyloside (RADIA EASYSURF 6505, commercially available from Oleon) and mixture of C5 Amyl, C8 Capryl, C12 Lauryl xylosides (RADIA EASYSURF 6552, commercially available from Oleon).

In one embodiment, suitable water-soluble co-solvents include, but are not limited to, ethanol, 1-propanol, 2-propanol, 1-butanol, 1,2-butanediol, 1,2-pentandiol 1,2-hexanediol, 1,2-heptanediol, 2-methyl-pentan-2,4-diol; glycol ethers, such as propylene glycol, dipropylene glycol, 1,3-propanediol, glycol esters and glycol ethers available commerically from Dow Chemicals under the name Dowanol®, such as Dowanol® DPMA (dipropylene glycol methyl ether acetate), Dowanol® DPM (dipropylene glycol methyl ether), Dowanol® TPM (tripropylene glycol methyl ether), Dowanol® DPNB (propylene glycol n-butyl ether, Dowanol® DPNP (propylene glycol n-propyl ether), and other suitable Dow Chemical P-series glycol ethers, methyl methoxy butanol, commercially available from Kuraray, (+/−)-2,2-dimethyl-4-hydroxymethyl-1,3-dioxolane, commercially available from Solvay under the name Augeo Clean Multi, dimethyl isosorbide, triethyl citrate and mixtures thereof.

In one embodiment, suitable water-insoluble or partially insoluble solvents include, but are not limited to, isopropyl myristate, methyl myristate, alkyl esters, such as methyl linoleate, methyl palmitate, ethyl laurate, ethyl linoleate, ethyl oleate, ethyl octanoate, dibenzyl ether and diethyl phthalate, dibasic ester DBE (blend composed of diisobutyl glutarate, diisobutyl succinate, and diisobutyl adipate, commercially available from Solvay, or blend composed of diisobutyl glutarate, and diisobutyl adipate, commercially available from Invista, and hydrocarbons, such as Isopar H, Isopar M and Isopar L, commercially available from Exxon.

In one embodiment, suitable preservatives include, but are not limited to, butylated hydroxyanisole (BHA), butylated hydroxytoluene (BHT), dilauryl thiodipropionate, alkyl parabene, tocopherols and the like. In another embodiment, a suitable preservative includes a combination of benzisothiazolone (BIT), methylisothiazolone (MIT) and/or laurylamine dipropylenediamine (BDA), and mixtures thereof, for example, Parmetol® MBX, commercially available from Schulke & Mayr, and the Acticide® series, commercially available from Thor Specialties, Inc.

In one embodiment, suitable deodorizing agents include, but are not limited to, zinc derivatives, essential oils, sodium undecylenate, methyl undecylenate, 2-hydroxypropyl beta cyclodextrin, soyethyl morpholinium ethosulfate, crotonates and fumarates, and alkylene carbonates.

In one embodiment, when the fragrance emitters are fully hydrated (swelled), the fragrance emitters may typically contain up to about 25% by weight of water absorbing polymer; in another embodiment up to about 20% by weight of the water absorbing polymer; in another embodiment up to about 15% by weight of the water absorbing polymer; in another embodiment up to about 10% by weight of the water absorbing polymer; in another embodiment up to about 7% by weight of the water absorbing polymer; and in yet another embodiment up to about 3% by weight of the water absorbing polymer. In another embodiment, the fragrance emitters contain up to about 15% by weight of the fragrance composition; in another embodiment up to about 10% by weight of the fragrance composition; and in another embodiment up to about 5% by weight of the fragrance composition, and in another embodiment up to about 3% by weight of the fragrance composition. In another embodiment, the fragrance emitters contain between about 3% and about 15% by weight of the fragrance composition; and in another embodiment between about 1% and about 10% by weight of the fragrance composition. In another embodiment, the fragrance emitters contain up to about 30% of at least one water-soluble co-solvent; in another embodiment between about 1% and about 30%, in another embodiment between about 3% and about 20%, and in yet another embodiment between about 5% and about 15% of water-soluble co-solvent. In another embodiment, the fragrance emitters contain up to about 10%, in another embodiment up to about 8%, and in yet another embodiment up to about 5% of at least one water-insoluble or partially soluble solvent. In another embodiment, the fragrance emitters contain between about 1% and about 20%, in another embodiment between about 3% and about 15%, and in yet another embodiment between about 5% and about 12% of at least one surfactant. In another embodiment, the fragrance emitters contain up to about 75% by weight of water; in another embodiment up to about 90% by weight of water; and in yet another embodiment up to about 99% by weight of water.

In another embodiment, the fragrance emitter may also contain other volatile active materials such as insecticides, insect repellant, herbals, medicinal substances, mood enhancers, aromatherapy compositions, and the like.

As described above, in one embodiment, the fragrance emitter according to the present disclosure is present in the form of a multitude of substantially individual fragranced water beads. In one embodiment, the water beads may be of a regular globular or elliptical or even square shape or of an irregular rounded shape. Using beads maximizes the surface area of the pieces and facilitates the release of the fragrance composition. In one embodiment, the beads may be contained in an open top container or tray of the air freshening device. This allows the device to be easily cleaned and refilled with beads.

In addition, the air freshening device according to the present disclosure includes a working signal and an end of life signal, i.e. the device provides users with multiple signals to indicate that the emitter is working and that essentially all of the fragrance composition has been delivered by the air freshening system. The use of such an end of life mechanism facilitates a user's understanding that the air freshening system should be refilled with a fresh supply of fragrance emitters.

In one embodiment, a plurality of water beads is placed within a warmer tray so as to be at least partially visible to a user. According to the present disclosure, a working signal is first conveyed to a consumer upon evaporation of both fragrance and water from the emitters. For example, the gradual transformation of the visual aspect of the emitter, from a transparent gel to an opaque gel, together with a gradual reduction of the size of the emitters.

Upon use, the water and the fragrance composition will evaporate from the water beads. With no more liquid composition to keep the beads wetted, the beads will begin to lose the liquid contained therein and shrink as the lost liquid evaporates from the device. The size of the beads will be reduced quite dramatically during this process of liquid loss therefrom, the beads being reduced in size to at least less than two to four times their swelled size. Advantageously, this reduction in bead size is easy for a user of the device to notice. According to the present disclosure, in one embodiment, the water beads will also undergo a color change when the fragrance composition is exhausted from the emitter. In one embodiment, the water beads may be translucent. In another embodiment, the water beads may be colored. For purposes of the present disclosure, a color change may include a change in the appearance of the water beads, for example, from transparent to opaque.

According to the present disclosure, an end of life signal occurs after evaporation of the fragrance composition and water. For purposes of the present disclosure, evaporation is when at least about 90% by weight of the fragrance composition and water have evaporated from the emitter. For example, the plurality of water beads are transformed from a soft gel material into a hard material. As a result, a user of the air freshening device according to the present disclosure is provided with a working signal (reduction in size of emitters and change in color of emitters) and an end of life signal (change of emitters from soft to hard) whereby the user clearly understands that replacement of the fragrance emitters is required.

Air freshening devices suitable for use with fragrance emitters in accordance with the present disclosure include warming devices or fragrance warmers, such as wax warmers and candle warmers. These devices typically include a power supply, a heating element, scented wax and a plate or container for the scented wax to be contained thereon. These devices are typically powered by mains electricity, batteries or with a tea light or votive candle. Any suitable size, shape, form, or configuration can be used. Suitable devices can be made from any suitable material, including but not limited to: natural materials, man-made materials, fibrous materials, non-fibrous materials, porous materials, non-porous materials, and combinations thereof.

Figure 1:
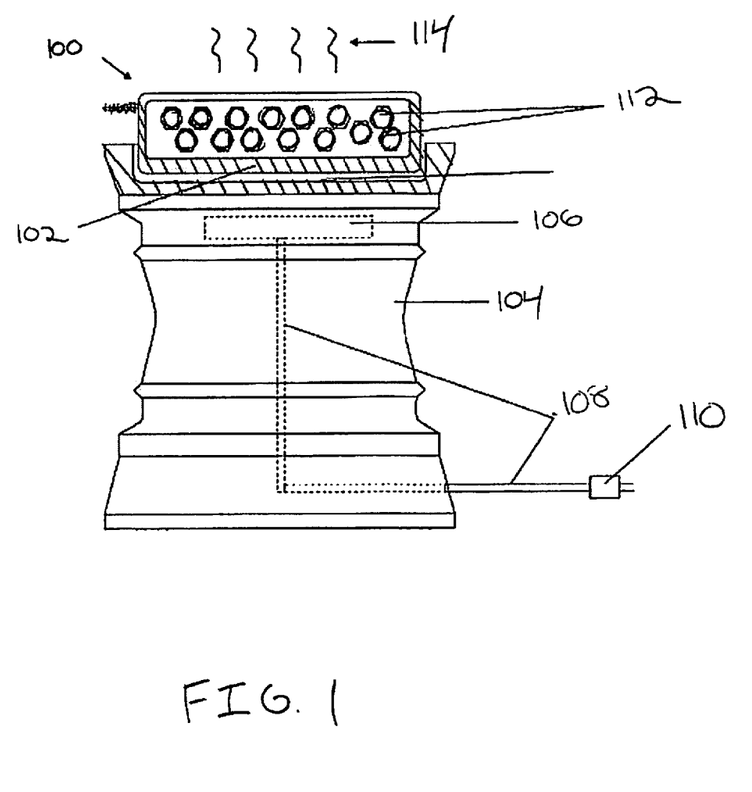
FIG. 1 is a perspective view of an air care device according to one or more embodiments illustrated and described herein.

In one embodiment, as shown in FIG. 1, a fragrance warmer 100 can be implemented as a fragrance lamp having a warmer body 104 configured to support a warmer tray 102. The warmer tray 102 may be heated with electricity or other means of heating. In one embodiment, the warmer tray 102 may include an electrical resistor 106 which may be in electrical communication with a power outlet via a power plug 108 and an electrical cord 110. The warmer tray 102 may be made of any heat conductive material, such as brass, aluminum, steel, copper, stainless steel, silver, tin, bronze, zinc, iron, clad materials, heat conductive polymers, ceramics, glass, or any other suitable heat conductive material or combination of such materials. Other heating elements are known in the art and are equally interchangeable with the non-limiting example provided here. Those of ordinary skill in the art can readily select appropriate materials for creating a warmer tray surface with a desired temperature. In particular embodiments, for safety reasons, the temperature of the fragrance warmer is designed so that it does not exceed 90° C.

As shown in FIG. 1, in operation, fragrance emitter 112 is placed in warmer tray 102 and the warmer tray 102 is then placed on warmer body 104 so that the warmer tray 102 is in thermal communication with the warmer body 104. In one embodiment, as the fragrance emitter is heated, it softens and a portion of the fragrance 114 is permitted to evaporate from the emitter. In one example, with the warmer tray surface at a temperature of about 50° C. to about 85° C., a fragrance composition may take less than six hours to evaporate. In another example, a fragrance composition may take less than four hours to evaporate. In yet another example, a fragrance composition may take less than two hours to evaporate. It will be understood that the time in which a portion of the fragrance evaporates may vary depending upon the temperature of the warmer tray, the size of the fragrance emitter, the amount of fragrance in the fragrance emitter, the ambient room temperature, and other factors.

EXAMPLES

The following examples are given solely for the purpose of illustration and are not to be construed as limitations of the present invention, as many variations of the invention are possible without departing from the spirit and scope of the present disclosure.

Example 1

A series of water-based emitters were prepared by using the compositions reported in Table 1 and mixtures of one top note (LINALOOL) and one bottom note (HEXYL CINNAMIC ALDEHYDE (HCA)), as example fragrance ingredients. The only variable from one emitter to the other was the top note to bottom note ratio, as listed in Table 2.

TABLE 1

| Fragrance Emitter | |
| --- | --- |
| Component | wt % |
| Mixture of Bottom Note[1] and Top Note[2] | 5.0 |
| Surfactant[3] | 10.0 |
| Organic Solvent[4] | 10.0 |
| Water Absorbing Polymer[5] | 2.5 |
| Water | quantity sufficient to 100% |

[1]HEXYL CINNAMIC ALDEHYDE (HCA) is a perfume material available from Kao Corporation (CAS Number 101-86-0)

[2]LINALOOL is a perfume material available from BASF (CAS Number 78-70-6)

[3]Neodol ® 91/8 is a primary alcohol ethoxylate available from Shell Chemicals

[4]Ethanol

[5]Hisobead ® is a bead-typed poly (acrylic acid) partial NA salt available from Aekyung Specialty Chemicals Ltd. (CAS 9033-79-8)

TABLE 2

Fragrance Compositions

| | Bottom Note[1] (parts per weight) | Top Note[2] (parts per weight) | Total |
|---|---|---|---|
| Mixture A | 30 | 70 | 100 |
| Mixture B | 50 | 50 | 100 |
| Mixture C | 70 | 30 | 100 |

[1]HEXYL CINNAMIC ALDEHYDE (HCA) is a perfume material available from Kao Corporation (CAS Number 101-86-0)
[2]LINALOOL is a perfume material available from BASF (CAS Number 78-70-6)

Figure 2:
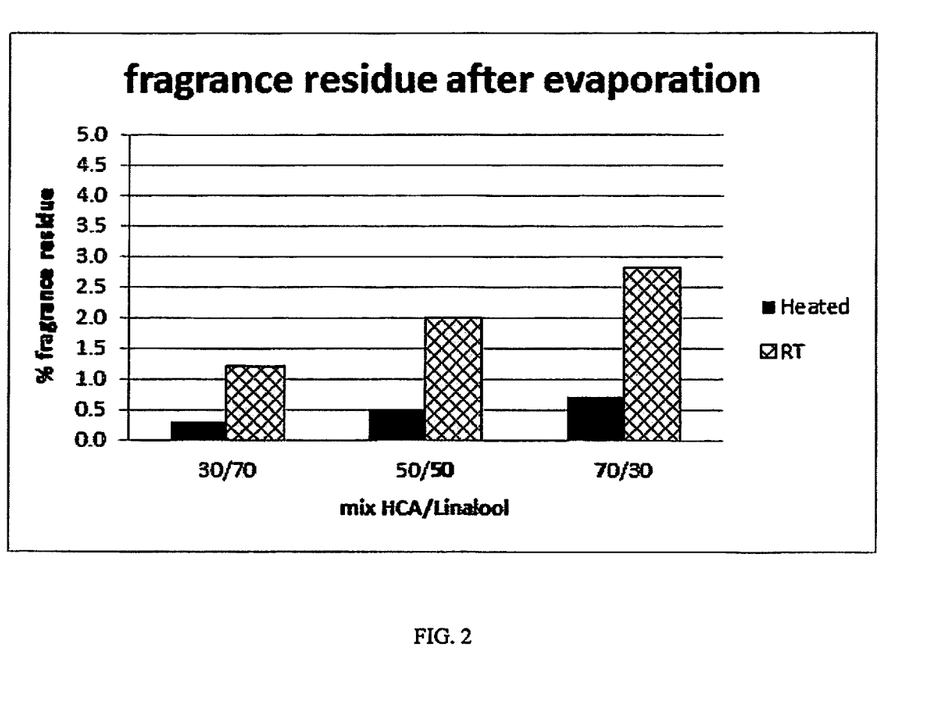
FIG. 2 is an evaporation comparison between mixtures of fragrance compositions as described in Example 1.

Fragrance compositions (Mixtures A-C) were weighed before and after 6 hours evaporation at room temperature (ca. 25° C.) (passive emission) and at ca. 70° C. (thermally activated emission). The samples that were activated thermally were put on a ceramic holder plate and heated with a tea light candle. The % of fragrance residue remaining (as related to the initial weight of the emitter) is reported in Table 3 and FIG. 2.

TABLE 3

| Bottom Note/Top Note ratio | % Fragrance residue after 6 days evaporation at room temperature | % Fragrance residue after 6 days evaporation at 70° C. |
|---|---|---|
| Mixture A -- 30/70 | 1.1 | 0.3 |
| Mixture B -- 50/50 | 2.0 | 0.5 |
| Mixture C -- 70/30 | 2.8 | 0.7 |

Table 3 (FIG. 2) demonstrates the benefit of heating the water-based fragrance emitters according to the present disclosure, i.e. the percentage of bottom note fragrance ingredients can be increased while at the same time maintaining a minimum amount of residual fragrance material remaining after the end of life of the emitter.

Example 2—Preparation of Different Types of Fragrance Emitters and Evaluation of Fragrance Intensity Three different fragrance emitters were prepared according to the compositions in Table 4: a wax-based fragrance emitter according to the prior art using SASOLWAX 6213 available from Sasol Limited (Comparative Product A); water-based fragrance emitters consisting of larger beads (3 to 3.5 mm diameter in the dry state, 8 to 11 mm diameter in the swollen state) (Product B according to the present disclosure); and water-based fragrance emitters consisting of small beads (1.7 to 2 mm diameter in the dry state, 5 to 5.1 mm diameter in the swollen state) (Product C according to the present disclosure). The diameter of the dry beads can be measured as follows: the beads are left to evaporate in a drying oven heated to 80° C. for 3 days; the size of approximately 10 beads is then measured using any length measuring device, such as a graduate ruler or a caliper. The average diameter is taken as representative diameter of the beads. These systems were let to evaporate at 70° C. on a ceramic holder heated by a tea light candle. The total amount of perfume in each of Products A, B and C was 0.4 grams.

TABLE 4

Fragrance Emitters

| Component | Comparative Product A | Product B | Product C |
|---|---|---|---|
| Matrix | Wax | SAP large beads | SAP small beads |
| Perfume[1] | 3.0 wt % | 3.0 wt % | 3.0 wt % |
| Surfactant[2] | — | 3.0 wt % | 3.0 wt % |
| Water-soluble co-solvent[3] | — | 10 wt % | 10 wt % |
| Water-partially soluble co-solvent[4] | 1.3 wt % | 1.3 wt % | 1.3 wt % |
| Water-insoluble solvent[5] | 2.7 wt % | 2.7 wt % | 2.7 wt % |
| Wax[6] | Quantity sufficient to 100% | — | — |
| SAP[7] | — | 2.5 wt % | 2.5 wt % |
| Water | — | Quantity sufficient to 100% | Quantity sufficient to 100% |

[1]Perfume composition comprising 3% Top Notes, 65% Middle Notes and 32% Bottom Notes
[2]Neodol ® 91/8 is a primary alcohol ethoxylate available from Shell Chemicals
[3]Ethanol
[4]Triethyl citrate
[5]Isopropyl myristate
[6]SASOLWAX 6213
[7]Hisobead ® is a bead-typed poly (acrylic acid) partial NA salt available from Aekyung Specialty Chemicals Ltd. (CAS 9033-79-8)

Products A, B and C were evaluated in a stainless steel smelling booth (23 m³) by a panel of 20 expert panelists who have been trained to rate the fragrance intensity and assign a score for intensity according to the following procedure: (i) the smelling booth air controller is set for exhaust (which removes air from the booth to outside the building) for fifteen minutes; (ii) a panelist verifies that there is not any residual fragrance or odor present in the booth. The booth air controller is set to the "off" position, which stops any air flow or air exchange within the booth (note: Relative Humidity and temperature are not controlled and can vary depending on the time of year); (iii) panelists enter the booth and close the door; (iv) a fragrance emitter is left to evaporate at 70° C. on a ceramic holder heated by a tea light candle; (v) panelists perform fragrance intensity evaluations over the next sixty seconds, making observations on intensity, character and distribution within the booth. All doors are closed upon exiting the booth and remain closed during the test period; (vi) the same panelists re-enter the booth, closing the door upon entry and perform intensity evaluations at 5 minutes, 10 minutes, and 15 minutes after the initial evaluation.

Figure 3:
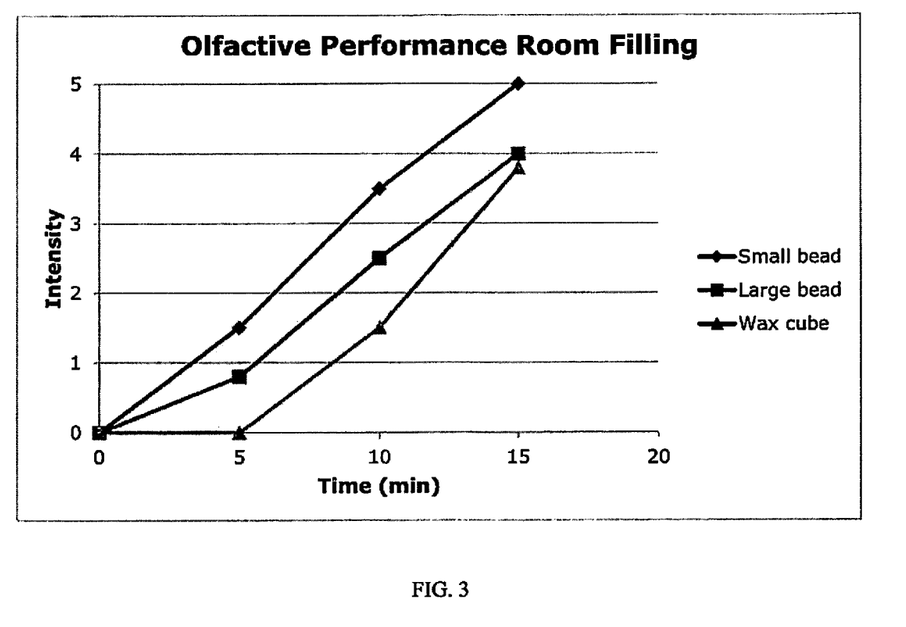
FIG. 3 is a fragrance intensity comparison between different fragrance emitters as described in Example 2.

The results were entered on a scale of from 0 to 5, wherein 0 is no smell; 1 is very weak, i.e. cannot smell in all parts of the booth; 2 is weak, i.e. can be smelled in all corners, still cannot recognize character; 3 is moderate, i.e. room filling, character clearly recognizable; 4 is strong, i.e. very room filling, but slightly overpowering; and 5 is very strong, i.e. extremely overpowering, permeates into nose. The results are shown below in Table 5 and FIG. 3. The results are recorded as an average of the panelists' scores.

TABLE 5

| | Comp. Product A | Product B | Product C |
|---|---|---|---|
| After 60 seconds | 0 | 0.1 | 0.3 |
| After 5 minutes | 0 | 0.9 | 1.5 |
| After 10 minutes | 1.2 | 2.6 | 3.5 |
| After 15 minutes | 3.9 | 4.0 | 5.0 |

The fragrance intensity of Products B and C are at all stages better than the intensity of the comparison product (Comp. Product A). The rate of fragrance room filling, i.e. the intensity of the smell in the room after a certain time, was significantly faster for Products B and C than that obtained with traditional wax-based fragrance emitter (Comp. Product A).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An air freshening device comprising: a water-based fragrance emitter including water, a water absorbing partially cross-linked hydrophilic copolymer selected from the group consisting of partially saponified (meth)acrylic acid, alkyl acrylates, hydroxyl alkyl acrylates and mixtures thereof, and a fragrance composition, the fragrance composition having from about 3% to about 70% by weight of at least one fragrance ingredient exhibiting a standard equilibrium headspace concentration ($HS_i^0$) below about 100 μg/L, from greater than 0% to about 50% by weight of at least one fragrance ingredient exhibiting a standard equilibrium headspace concentration ($HS_i^0$) greater than about 1000 μg/L, or from 30% to about 97% by weight of at least one fragrance ingredient exhibiting a standard equilibrium headspace concentration ($HS_i^0$) about 100 μg/L to about 1000 μg/L.

2. The air freshening device according to claim 1, wherein the water-based fragrance emitter comprises a plurality of water beads.

3. The air freshening device according to claim 1, wherein the water-based fragrance emitter provides a working signal and an end of life signal upon evaporation.

4. The air freshening device according to claim 1, wherein the air freshening device is a warming device.

5. The air freshening device according to claim 1, further comprising from greater than 0% to about 50% by weight of at least a second fragrance ingredient exhibiting a standard equilibrium headspace concentration ($HS_i^0$) above about 1000 μg/L.

6. The air freshening device according to claim 3, wherein the working signal is selected from color change and size reduction.

7. The air freshening device according to claim 1, wherein the water-based fragrance emitter includes up to about 5% by weight of the water absorbing polymer and up to about 15% by weight of the fragrance composition.

8. The air freshening device according to claim 1, wherein the fragrance composition comprising from about 5% to about 50% by weight of at least one fragrance ingredient exhibiting a standard equilibrium headspace concentration ($HS_i^0$) below about 100 μg/L.

9. The air freshening device according to claim 1, wherein the fragrance composition includes from about 10% to about 35% by weight of at least one fragrance ingredient exhibiting a standard equilibrium headspace concentration ($HS_i^0$) below about 100 μg/L.

10. The air freshening device according to claim 1, wherein upon evaporation the amount of fragrance residue remaining in the device is less than about 1.0% by weight of the emitter.

11. The air freshening device according to claim 1, wherein the fragrance emitter has a fragrance intensity of greater than about 1 on a scale of from zero to five after 5 minutes.

12. The air freshening device according to claim 1, wherein the fragrance emitter has a fragrance intensity score of at least 2 on a scale of from zero to five after 10 minutes.

13. An air freshening device according to claim 1, wherein the fragrance emitter includes up to about 15% by weight of the fragrance composition.

14. The air freshening device according to claim 2, wherein the plurality of beads have a diameter in the dry state of from about 1.5 mm to about 4.0 mm.

15. The air freshening device according to claim 1, wherein upon evaporation, the water-based fragrance emitter is easily removable from the device.

16. The air freshening device according to claim 1, wherein the at least one fragrance ingredient is selected from the group consisting of 1,1,2,3,3-pentamethyl-2,3,6,7-tetrahydro-1H-inden-4(5H)-one; 4,6,6,7,8,8-hexamethyl-1,3,4,6,7,8-hexahydrocyclopenta[g]isochromene; ((4 S)-4,6,6,7,8,8-hexamethyl-1,3,4,6,7,8-hexahydrocyclopenta[g]-2-benzopyran); 1a,3,3,4,6,6-hexamethyl-1a,2,3,4,5,6,7,7a-octahydronaphtho[2,3-b]oxirene; (Z)-3-methylcyclotetradec-5-enone; oxacyclohexadecan-2-one; (Z)-cyclohexadec-5-enone; (Z)-3-methylcyclopentadec-5-enone; (E)-13-methyloxacyclopentadec-10-en-2-one; (E)-oxacyclohexadec-12-en-2-one; (Z)-cycloheptadec-9-enone; 1,4-dioxacyclohexadecane-5,16-dione; 1,4-dioxacycloheptadecane-5,17-dione; (Z)-oxacycloheptadec-10-en-2-one; 2-(1-(3,3-dimethylcyclohexyl)ethoxy)-2-methylpropyl cyclopropanecarboxylate; (E)-2-((3,5-dim ethylhex-3-en-2-yl)oxy)-2-methylpropyl cyclopropanecarboxylate; blend of cyclopentadecanone and cyclohexadecanolide; 3,7-dimethyloct-6-en-1-yl ethyl oxalate; 2-[1-(3,3-dimethylcyclohexyl)ethoxy]-2-methylpropyl]propanoate; 1-3,3-dimethyl cyclohexyl)ethoxy)carbonyl)methyl propionate; Pentambrette; propanedioic acid 1-(3,3-dimethylcyclohexyl)ethyl ethyl ester; 1-(3,3-dimethylcyclohexyl)ethyl acetate; 2-(2,2-dim ethyl-3-propionyl)-1-methyl-3-(methyl ethenyl)cyclopentene; (E)-2-methoxy-4-(prop-1-en-1-yl)phenyl acetate; 4-formyl-2-methoxyphenyl acetate; 1-((2-(tert-butyl)cyclohexyl)oxy)butan-2-ol; dodecahydrotetramethyl epoxynaphthoxepin; 3,8,8,11a-tetramethyldodecahydro-1H-3,5a-epoxynaphtho[2,1-c]oxepine; (2,4a,5,8a-tetramethyl-1,2,3,4,7,8-hexahydronaphthalen-1-yl) formate; (4aR,5R,7aS,9R)-octahydro-2,2,5,8,8,9a-hexamethyl-4h-4a,9-methanoazuleno(5,6-d)-1,3-dioxole; 3a,6,6,9a-tetramethyldodecahydronaphtho[2,1-b]furan; 3a,6,6,9a-tetramethyldodecahydronaphtho[2,1-b]furan; ((1S,8aR)-1,4,4-trimethyl-2,3,3a,4,5,8-hexahydro-1H-5,8a-methanoazulen-6-yl)methanol; 7-isopentyl-2H-benzo[b][1,4]dioxepin-3(4H)-one; 4-(1,3-benzodioxol-5-yl)butan-2- one; (1S,6R,8aR)-1,4,4,6-tetramethyloctahydro-1H-5,8a-methanoazulen-6-ol; (1S,6R,8aR)-1,4,4,6-tetramethyloctahydro-1H-5,8a-methanoazulen-6-yl acetate; methyl 2,4-dihydroxy-3-methylbenzoate; 3-phenylprop-2-enoicacid; 2-hydroxy-3-methylcycloent-2-enone; 2H-chromen-2-one; p-tolyl 2-phenyl acetate; 3-phenylprop-2-enyl 3-phenylprop-2-enoate; 2-ethyl-3-hydroxy-4H-pyran-4-one; 3-ethoxy-4-hydroxybenzaldehyde; methyl 2,4-dihydroxy-3,6-dimethylbenzoate; methyl 2-(3-oxo-2-pentylcyclopentyl)acetate; 2-ethyl-4-hydroxy-5-methylfuran-3(2H)-one; 1H-indole; 3-hydroxy-2-methyl-4H-pyran-4-one; hexyl (E)-3-phenylprop-2-enoate; 2-methylundecanoic acid; 2-ethoxynaphthalene; 1-naphthalen-2-ylethanone; 3-methoxy-5-methylphenol; 2-cyclohexylidene-2-phenylacetonitrile; 2-phenylacetic acid; 2-phenethyl cinnamate; (E)-2-benzylideneoctanal; phenethyl 2-hydroxybenzoate; 4-hydroxy-3-methoxybenzaldehyde; 2-methoxynaphthalene and mixtures thereof.

17. The air freshening device according to claim 1, wherein the fragrance composition comprises from about 3% to about 70% by weight of at least one fragrance ingredient exhibiting a standard equilibrium headspace concentration ($HS_i^0$) below about 100 μg/L.

18. The air freshening device according to claim 1, wherein the fragrance composition comprises from greater than 0% to about 50% by weight of at least one fragrance ingredient exhibiting a standard equilibrium headspace concentration ($HS_i^0$) greater than about 1000 μg/L.

19. The air freshening device according to claim 1, wherein the fragrance composition comprises from 30% to about 97% by weight of at least one fragrance ingredient exhibiting a standard equilibrium headspace concentration ($HS_i^0$) about 100 μg/L to about 1000 μg/L.

20. The air freshening device according to claim 1, wherein the fragrance emitter comprises at least one of surfactants, water-soluble co-solvents, water-insoluble or partially soluble co-solvents, preservatives, deodorizing agents, insecticides, insect repellant, herbals, medicinal substances, mood enhancers or aroma therapy compositions.

* * * * *